(12) United States Patent
Jones et al.

(10) Patent No.: US 8,740,873 B2
(45) Date of Patent: *Jun. 3, 2014

(54) SOFT BODY CATHETER WITH LOW FRICTION LUMEN

(75) Inventors: Michael L. Jones, San Clemente, CA (US); Frank R. Louw, Carlsbad, CA (US)

(73) Assignee: Hologic, Inc., Bedford, MA (US)

( * ) Notice: Subject to any disclaimer, the term of this patent is extended or adjusted under 35 U.S.C. 154(b) by 684 days.

This patent is subject to a terminal disclaimer.

(21) Appl. No.: 11/724,578

(22) Filed: Mar. 15, 2007

(65) Prior Publication Data

US 2008/0228150 A1 Sep. 18, 2008

(51) Int. Cl.
*A61M 25/00* (2006.01)

(52) U.S. Cl.
USPC .............................. 604/523; 600/4

(58) Field of Classification Search
USPC .............................. 604/523; 600/4
See application file for complete search history.

(56) References Cited

U.S. PATENT DOCUMENTS

| | | | |
|---|---|---|---|
| 3,324,847 A | | 10/1964 | Zoumboulis |
| 3,872,856 A | | 3/1975 | Clayton |
| 3,975,350 A | * | 8/1976 | Hudgin et al. ............. 524/108 |
| 4,119,094 A | * | 10/1978 | Micklus et al. ............. 128/844 |
| 5,106,360 A | | 4/1992 | Ishiwara et al. |
| 5,167,622 A | | 12/1992 | Muto |
| 5,312,356 A | * | 5/1994 | Engelson et al. ........ 604/164.13 |
| 5,342,305 A | | 8/1994 | Shonk |
| 5,381,504 A | | 1/1995 | Novack et al. |
| 5,417,687 A | | 5/1995 | Nardella et al. |
| 5,429,582 A | | 7/1995 | Williams |
| 5,603,991 A | | 2/1997 | Kupiecki et al. |
| 5,611,767 A | | 3/1997 | Williams |
| 5,662,580 A | | 9/1997 | Bradshaw et al. |
| 5,704,926 A | * | 1/1998 | Sutton ......................... 604/526 |

(Continued)

FOREIGN PATENT DOCUMENTS

| | | |
|---|---|---|
| EP | O 536 440 | 4/1993 |
| EP | 0 642 766 | 3/1995 |

(Continued)

OTHER PUBLICATIONS

Gregory K. Edmundson, M.Sc., et al., "Dosimetric Characteristics of the Mammosite RTS, A New Breast Brachytherapy Applicator", Int. J. Radiation Oncology Biol., vol. 52, No. 4, pp. 1132-1139, 2002.

(Continued)

*Primary Examiner* — Emily Schmidt

(57) ABSTRACT

The disclosure is directed to radiation catheter devices, methods for controlled application of irradiation to tissue at a body site, such as a cavity formed after removal of tissue, e.g. cancer, using such radiation catheter devices, solutions for forming a more lubricious luminal surface and method for lining lumens of such devices to improve the frictional characteristics thereof. The catheter device includes a flexible elongated shaft which is formed of low durometer polymeric material, which can be readily folded or coiled for securing the shaft to or under the skin of the patient and a radiation lumen lined with high durometer polymeric material to improve the frictional characteristics. The elongated shaft has at least one inner lumen for receiving a radiation source which has a layer of high durometer polymeric material that provides lower surface friction to facilitate advancement of a radiation source therein.

22 Claims, 3 Drawing Sheets

(56) References Cited

U.S. PATENT DOCUMENTS

| | | | |
|---|---|---|---|
| 5,720,717 | A | 2/1998 | D'Andrea |
| 5,759,173 | A | 6/1998 | Preissman et al. |
| 5,820,594 | A | 10/1998 | Fontirroche et al. |
| 5,863,285 | A | 1/1999 | Coletti |
| 5,913,813 | A | 6/1999 | Williams et al. |
| 5,931,774 | A | 8/1999 | Williams et al. |
| 5,935,098 | A | 8/1999 | Blaisdell et al. |
| 5,993,972 | A * | 11/1999 | Reich et al. ............... 428/423.1 |
| 6,022,308 | A | 2/2000 | Williams |
| 6,083,148 | A | 7/2000 | Williams |
| 6,086,970 | A * | 7/2000 | Ren ............................ 428/36.9 |
| 6,217,565 | B1 * | 4/2001 | Cohen .......................... 604/525 |
| 6,251,059 | B1 | 6/2001 | Apple et al. |
| 6,378,137 | B1 * | 4/2002 | Hassan et al. ................... 2/161.7 |
| 6,398,708 | B1 | 6/2002 | Hastings et al. |
| 6,413,203 | B1 | 7/2002 | Sahatjian |
| 6,413,204 | B1 | 7/2002 | Winkler et al. |
| 6,458,069 | B1 | 10/2002 | Tam et al. |
| 6,482,142 | B1 | 11/2002 | Winkler et al. |
| 6,527,693 | B2 | 3/2003 | Munro, III et al. |
| 6,540,655 | B1 | 4/2003 | Chin et al. |
| 6,673,006 | B2 | 1/2004 | Winkler |
| 6,752,752 | B2 | 6/2004 | Geitz |
| 6,923,754 | B2 * | 8/2005 | Lubock ............................ 600/3 |
| 6,955,641 | B2 | 10/2005 | Lubock |
| 7,214,178 | B2 | 5/2007 | Lubock |
| 7,322,929 | B2 | 1/2008 | Lovoi |
| 2001/0016725 | A1 | 8/2001 | Valley et al. |
| 2001/0049464 | A1 | 12/2001 | Ganz |
| 2001/0051669 | A1 | 12/2001 | McGhee |
| 2002/0045893 | A1 | 4/2002 | Lane et al. |
| 2002/0095114 | A1 | 7/2002 | Palasis |
| 2002/0177804 | A1 | 11/2002 | Saab |
| 2004/0039437 | A1 | 2/2004 | Sparer et al. |
| 2004/0087827 | A1 | 5/2004 | Lubock |
| 2004/0116767 | A1 | 6/2004 | Lebovic et al. |
| 2004/0215048 | A1 | 10/2004 | Lubock |
| 2005/0061771 | A1 | 3/2005 | Murphy |
| 2005/0080313 | A1 | 4/2005 | Stewart et al. |
| 2005/0124843 | A1 | 6/2005 | Singh |
| 2005/0182286 | A1 | 8/2005 | Lubock |
| 2005/0240074 | A1 | 10/2005 | Lubock |
| 2006/0100475 | A1 * | 5/2006 | White et al. ....................... 600/3 |
| 2006/0116546 | A1 | 6/2006 | Eng |
| 2006/0136051 | A1 * | 6/2006 | Furst et al. .................... 623/1.42 |
| 2006/0173233 | A1 | 8/2006 | Lovoi |
| 2007/0005003 | A1 * | 1/2007 | Patterson et al. ................ 604/43 |
| 2007/0270627 | A1 | 11/2007 | Cutrer et al. |
| 2008/0057298 | A1 * | 3/2008 | Finley ............................ 428/327 |

FOREIGN PATENT DOCUMENTS

| | | |
|---|---|---|
| EP | 0 693 293 | 1/1996 |
| EP | 0 719 571 | 7/1996 |
| EP | 0 853 957 | 7/1998 |
| EP | 0867 200 | 9/1998 |
| EP | 1 051 990 | 11/2000 |
| EP | 1 402 922 | 3/2004 |
| EP | 1 618 924 | 1/2006 |
| WO | WO 95/20241 | 7/1995 |
| WO | WO 97/45053 | 12/1997 |
| WO | WO 01/14011 | 3/2001 |
| WO | WO 01/43826 | 6/2001 |
| WO | WO 01/58346 | 8/2001 |
| WO | WO 02/09599 | 2/2002 |
| WO | WO 02/069862 | 9/2002 |
| WO | WO 2004/043531 | 5/2004 |
| WO | WO 2005/037363 | 4/2005 |
| WO | WO 2005/039665 | 5/2005 |
| WO | WO 2005/067442 | 7/2005 |
| WO | WO 2007/027831 | 3/2007 |
| WO | WO 2007/143560 | 12/2007 |

OTHER PUBLICATIONS

Melvin A. Astrahan, et al., "Optimization of Mammosite Therapy", Int. J. Radiation Oncology Biol., vol. 58, No. 1, pp. 220-232, 2004.

Philip H. Gutin et al., "A coaxial catheter system for afterloading radioactive sources for the interstitial irradiation of brain tumors", J. Neurosurg., vol. 56: pp. 734-735, May 1982.

International Search Report for PCT/US2006/043891 mailed Sep. 25, 2007.

Partial International Search Report for PCT/US2008/003364 mailed Jun. 30, 2008.

XP007904995:retrieved from the Internet: URL: http://www2.dupont.com/Teflon_Industrial/en_US/assets/downloads/h88800.pdf.

International Search Report of PCT/US2008/003364 mailed Aug. 27, 2008.

Written Opinion of the International Searching Authority of PCT/US2008/003364 mailed Aug. 27, 2008.

Paul V. Harper, "Some Therapeutic Applications of Radioisotopes", *Journal of the Mississippi State Medical Association*, Oct. 1966, vol. VII, pp. 526-533.

International Search Report of PCT/US2009/000402 mailed Apr. 15, 2009.

* cited by examiner

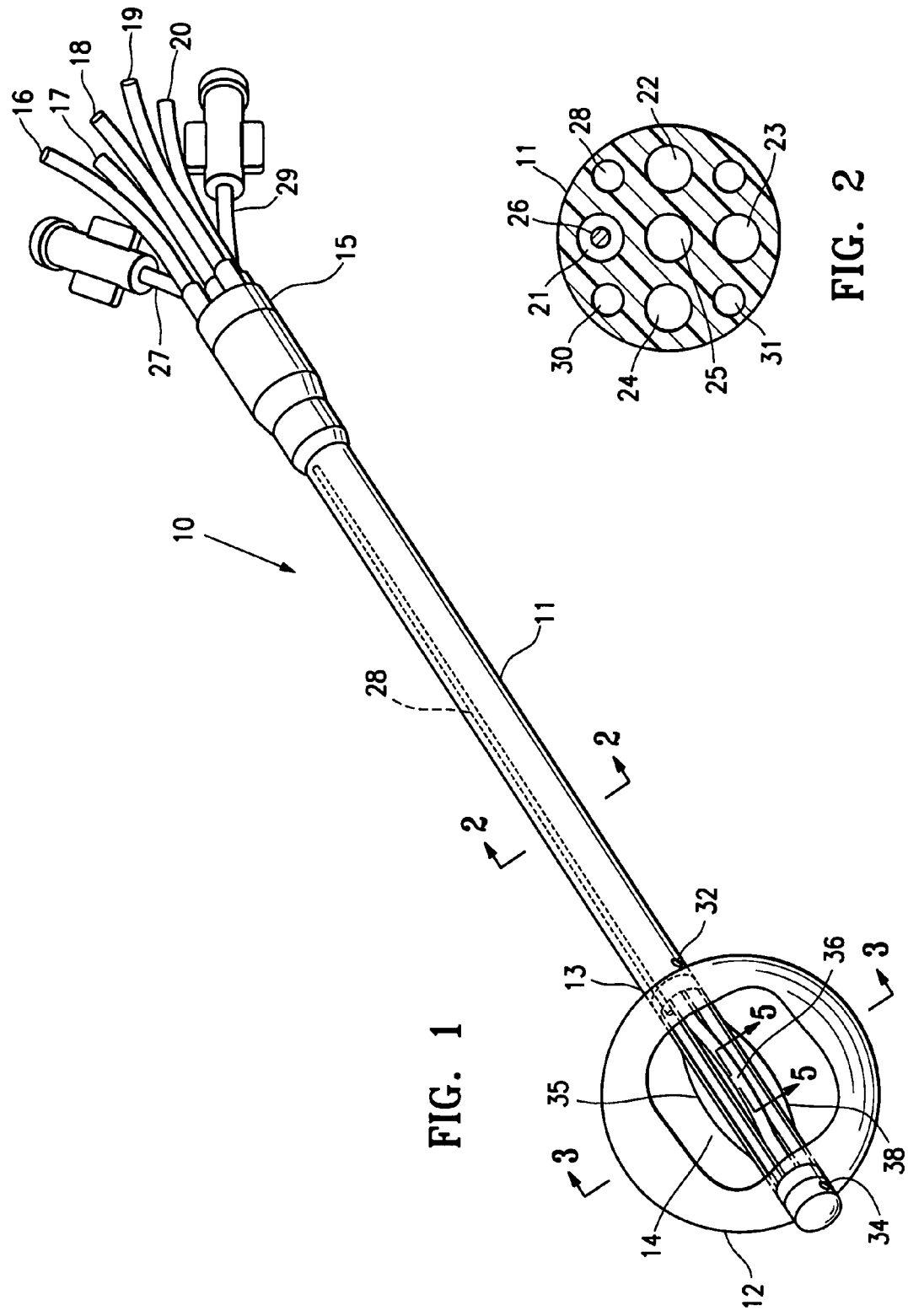

SOFT BODY CATHETER WITH LOW FRICTION LUMEN

FIELD OF THE INVENTION

This invention relates generally to the fields of medical treatment devices and methods of use. In particular, the invention relates to devices and methods for irradiating tissue surrounding a body cavity, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver irradiation to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., lotrex®, Proxima Therapeutics, Inc.). A radiation source such as a miniature or micro-miniature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

Tissue cavities resulting from biopsy or other surgical procedures such as lumpectomy typically are not always uniform or regular in their sizes and shapes, so that radiation treatment often result in differences in dosages applied to different regions of surrounding tissue, including "hot spots" and regions of relatively low dosage. However, by conforming the tissue lining the cavity about an inflated member, such as a balloon, a more uniform or controlled radiation can be applied to the tissue.

The radiation balloon catheter is usually retained within the patient for about 5-10 days during which time radiation is emitted from a radiation source within the balloon. The proximal end of the catheter is preferably folded or coiled and secured onto or under the patient's skin during the retention period. However, in order to facilitate folding or coiling the catheter shaft, the shaft must be fairly flexible or it will be difficult to maintain in the folded or coiled configuration without subjecting the patient to discomfort. The catheter shaft is formed of low durometer polymeric material in order to improve flexibility but low durometer polymeric materials have high friction surfaces, making advancing a radiation source through a lumen of the catheter shaft difficult. Forming a soft polymeric material about a single tube with a lumen with greater lubricity is not difficult but forming a soft polymeric material with a plurality of lumens with greater lubricity is problematic.

SUMMARY OF THE INVENTION

This invention is generally directed to irradiating tissue surrounding a patient's body cavity, and particularly to devices and methods for such treatments. The invention is particularly suitable for treating tissue adjacent a patient's body site such as a cavity formed by removal of tissue for a biopsy or lumpectomy.

More specifically, an elongated catheter device embodying features of the invention includes a flexible elongated shaft, a treatment location at a distal portion of the device, at least one lumen extending within the shaft to the treatment location which is configured to receive or which includes a radiation source. Preferably, the catheter has an inflatable cavity filling member or balloon surrounding the treatment location on the distal portion of the catheter. In this embodiment, the flexible elongated shaft is formed of relatively low durometer polymeric material, e.g. 70A to about 25D Shore Hardness, to provide flexibility. At least one, and preferably a plurality of the inner lumens are provided with a lining of relatively high durometer polymeric material, e.g. 40D to 80D Shore Hardness. The relatively low durometer polymeric material for the elongated shaft is preferably a thermoplastic elastomer such as polyurethane, e.g. Pellethane™ which is available from Dow Chemical. Other suitable polymeric material for lining the lumens include polyvinyl chloride, Styrene, ABS and other solvent dissolvable polymers. The polymeric material of the elongated shaft may be a blend or copolymer.

The lining of higher durometer polymeric material is preferably applied by dissolving the higher durometer polymeric material in a suitable non-aqueous solvent, e.g. tetrahydrofuran, applying the solution to the surface of the inner lumen and then evaporating the solvent to leave the higher durometer material on the surface of the lumen. Other solvents include cyclohexanone, dimethyl formamide and mixtures thereof. Other suitable combinations of high durometer polymers and non-aqueous solvents which dissolve such polymers may be employed.

A radiation catheter device embodying features of the invention preferably has one or more inner lumens configured to be in fluid communication with a proximal vacuum source and one or more vacuum ports preferably proximal and/or distal to the cavity filling member such as described in U.S. Pat. No. 6,923,754 and co-pending application Ser. No. 10/849,410, filed on May 19, 2004, both of which are assigned to the present assignee. Application of a vacuum within the inner lumen aspirates fluid in the cavity through the one or more vacuum ports and the application of a vacuum within the body cavity pulls tissue defining the cavity onto the exterior of the inflated cavity filling member deployed within the cavity so as to conform the tissue lining to the shape of the cavity filling member.

Methods previously described in co-pending application Ser. No. 11/357,274, filed on Feb. 17, 2006 and Ser. No. 11/593,789, filed on Nov. 6, 2006 for using radiation catheters are suitable for a radiation catheter embodying features of the invention body cavity.

The present invention provides a radiation catheter having a flexible shaft to facilitate securing the shaft to or under the patient's skin in a coiled or folded configuration and a low friction lumen for advancement of a radiation source to the treatment location of the shaft. The catheter is particularly suitable for treating a cavity created by breast biopsy or lumpectomy. These and other advantages of the present invention are described in more detail in the following detailed description and the accompanying exemplary drawings.

BRIEF DESCRIPTION OF THE DRAWINGS

FIG. 1 is a perspective view of a catheter device embodying features of the invention.

FIG. 2 is a transverse cross section of the catheter shaft taken along the lines 2-2 shown in FIG. 1.

DETAILED DESCRIPTION OF THE INVENTION

Figure 3:
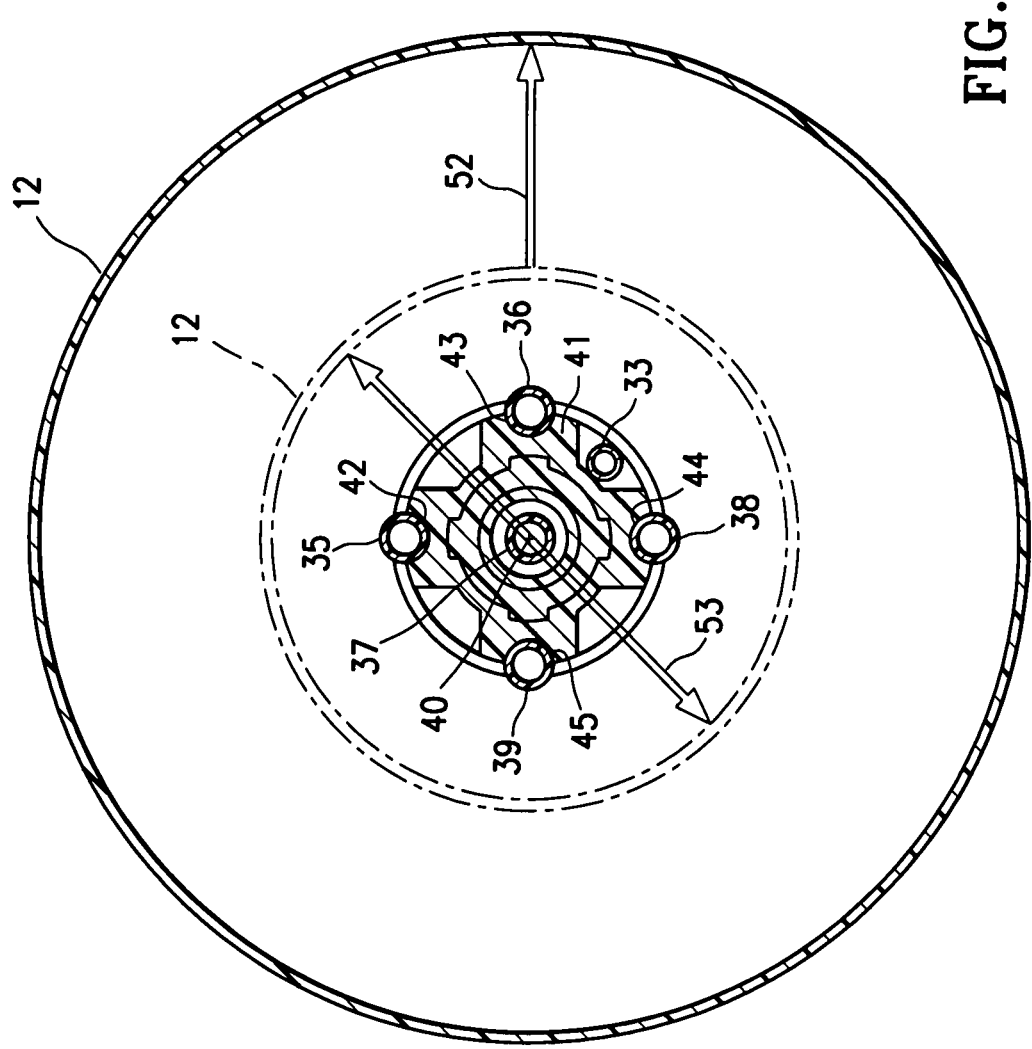
FIG. 3 is an enlarged transverse cross sectional view of the balloon shown in FIG. 1.
Figure 4A:
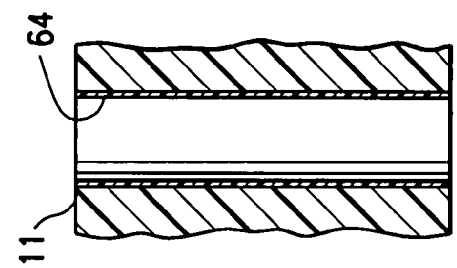
FIGS. 4A-4D are enlarged longitudinal sectional views of the flexible catheter shaft shown in FIG. 1-3 to illustrate the application of a high durometer coating to the surface of an inner lumen thereof.
Figure 4B:
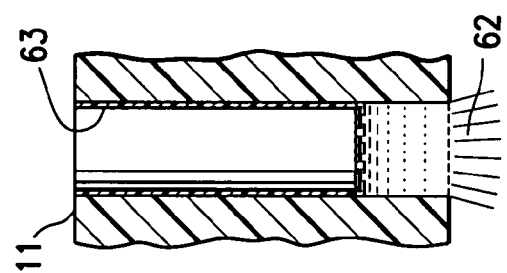
Figure 4C:
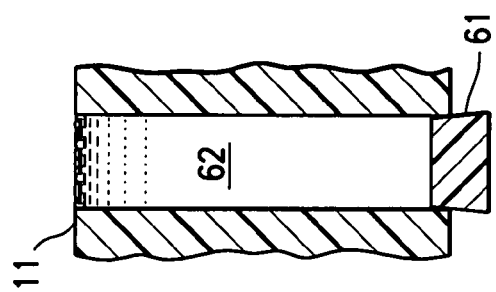
Figure 4D:
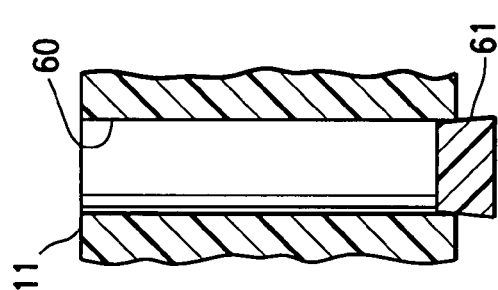
Figure 5:
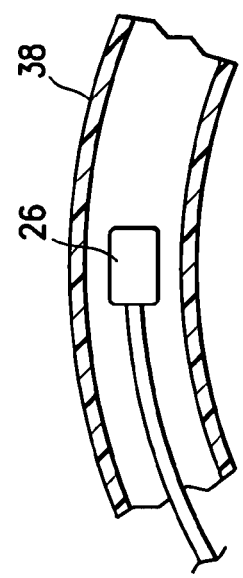
FIG. 5 is an enlarged longitudinal cross-section of a radiation tube taken along the lines 5-5 shown in FIG. 1 to illustrate the deployment of a radiation source within the treatment location.

FIGS. 1-5 illustrate an elongated catheter device 10 which has an elongated flexible shaft 11, an inflatable cavity filling member or balloon 12 on the distal portion 13 of the catheter which for the most part defines the treatment location 14, and an adapter 15 on the proximal end of shaft 11. A plurality of tubes 16-20 extend into the adapter 15 and are in fluid communication with lumens 21-25 respectively within the shaft 11 which are configured to receive one or more radiation sources 26. The catheter device 10 also has an inflation tube 27 which is in fluid communication with inflation lumen 28 in shaft 11 that extends to and is in fluid communication with the interior of the balloon 12 to facilitate delivery of inflation fluid thereto. The adapter 15 also has a vacuum tube 29 that is in fluid communication with lumens 30 and 31. Lumen 30 is in fluid communication with proximal vacuum port 32 and lumen 31 is in fluid communication with tubular member 33 which extends across the interior of balloon 12 and which in turn is in fluid communication with distal vacuum port 34. Radiation delivery tubes 35-39 extend through the interior of balloon 12 and are in fluid communication with lumens 21-25 within shaft 11. The radiation delivery tubes 35, 36, 38 and 39 extend radially away from a center-line axis 40 within the interior of balloon 12 in order to position a radiation source 26 closer to a first tissue portion surrounding a body cavity than a second tissue portion. While tubes 35, 36, 38 and 39 are shown as being slightly radially extended within the interior of balloon 12, less than all of them may radially extend within the balloon 12 depending upon the need for a particular treatment. Moreover, tubes 35, 36, 38 and 39 may be in a contracted state within recesses of a support member 41 which extends between the proximal and distal ends of the balloon 12, and one or more of the tubes may be radially extended out of the recesses after the balloon 12 is deployed within a cavity at the target body site. FIG. 5 illustrates the radiation source 26 disposed within the tube 38.

The support element 41 has four compartments 42-45 which are designed to receive tubular radiation delivery members 35, 36, 38 and 39 respectively. The radiation delivery tubes will not usually be radially extended to the extent that they contact the interior surface of the balloon 12 in an inflated condition.

The expansion of the balloon 12 is illustrated in FIG. 2 with the balloon in an as formed, non-turgid condition shown in phantom. The arrow 52 illustrates the expansion of the balloon to the turgid condition from the initial diameter shown as arrow 53. As described in co-pending application Serial No., filed on Mar. 12, 2007, entitled RADIATION CATHETER WITH MULTI-LAYERED BALLOON (Atty. Docket No. R0367-06900) the balloon is preferably multilayered and has an expansion from the un-inflated to turgid condition of less than 200%, preferably less than 175% of the initial diameter. While the inflated, turgid balloon 12 is shown as being spherical in shape, other shapes may be suitable, such as an ovoid shape. The thicknesses of the balloon wall layers can vary depending upon the material characteristics and the number of layers. Typically, the thickness of individual balloon wall layers range from about 0.0005 to about 0.006, preferably about 0.001 to about 0.003 inch.

FIGS. 4A-4D schematically illustrate lining a lumen 60, e.g. lumens 21-25, of flexible catheter shaft 11 with a high durometer polymeric material. As shown in FIG. 4A, the catheter shaft 11 is oriented vertically with a plug 61 blocking the lower opening to the lumen 60. The lumen 60 is filled with a solution 62 comprising a non-aqueous solvent and a high durometer polymeric solute as shown in FIG. 4B. The plug 61 is removed from the lower opening to lumen 60 as shown in FIG. 4C allowing the solution 62 to drain from the lumen leaving a thin layer 63 of solution on the wall of the lumen. The non-aqueous solvent is evaporated from the thin layer 63 of solution lining the lumen 60, leaving a coating 64 of the high durometer polymeric solute on the surface of the lumen as shown in FIG. 4D.

EXAMPLE

About 1.4 grams of a high durometer polyester polyurethane polymer (Pellethane™) having a durometer hardness of 65D Shore was dissolved in 90 ml of tetrahydrofuran which is a non-aqueous solvent. A flexible catheter shaft having a plurality of lumens and formed of relatively low durometer polyurethane was positioned vertically with the lower lumen openings closed off by a plug as shown in FIG. 4A. One or more lumens were filled with the solution of tetrahydorfuran and polyurethane polymer, the plugs removed and the solution gravity drained from the lumens. The solution remaining on the surface of the lumens was allowed dry, evaporating the solvent and leaving the high durometer polyurethane solute tenaciously lining the lumens. The lumens lined with the high durometer polyurethane material had lower friction coefficients than the lumens of the tubular member before lining with high durometer polyurethane. Brachytherapy seeds could be readily advanced through the lined lumens, whereas advancement through the lumens before the application of the lining was difficult.

If desired, a colorant such as an ink, dye or pigment may be added to the polymeric coating to aid in identifying one or more lumens. Friction reducing compounds such a zinc stearate (a mold release agent), surfactants such a polyvinyl alcohol or lubricants such as Carnauba wax may also be added to the coating. Except for pigments, such additives should be at least partially soluble in the solvent.

Pigments such as Reactive Blue, Prussian Blue, iron oxide, titanium dioxide, manganese violet, ultramarine blue and others may be suspended in the polymer solution to be deposited with the polymeric material. The pigment particles provide an undulating or uneven surface which reduces contact with the brachytherapy seed and the friction between the seed and the coating.

In one series of tests a lumen in a catheter shaft formed of a polyurethane having an 80A Shore Hardness was lined with a polyurethane having a 55D Shore Hardness as described above. The lined lumen exhibited a reduction of 75% of the force required to advance a brachytherapy seed through the lumen over an uncoated lumen of the same material. Incorporating Reactive Blue pigment into the polyurethane coating reduced the force required to advance the Brachytherapy seed through the lumen by almost 90% of the force required to advance the seed through an uncoated lumen of the same material.

All of the radiation delivery tubes which extend through the interior of the balloon 12 would not necessarily be used in a particular irradiation procedure, but they would be available for use by the physician if needed, e.g. when the balloon 12 of the radiation catheter 10 is not in a desired position and rotation of the catheter is not appropriate or desirable.

The radiation source 26 for the brachytherapy device 10 is shown as a radiation seed on the distal end of rod 41. The radiation source 26 preferably includes brachytherapy seeds or other solid radiation sources used in radiation therapy. A micro-miniature x-ray catheter may also be utilized. The radiation source 26 may be either preloaded into the device 10 at the time of manufacture or may be loaded into the device 10 just before or after placement into a body cavity or other site of a patient. Solid radionuclides suitable for use with a device 10 embodying features of the present invention are currently generally available as brachytherapy radiation sources (e.g., I-Plant. TM. Med-Tec, Orange City, Iowa.). Radiation may also be delivered by a micro-miniature x-ray catheter device such as described in U.S. Pat. No. 6,319,188. The x-ray catheter devices are small, flexible and are believed to be maneuverable enough to reach the desired location within a patient's body.

The radiation source 26 preferably is one or more brachytherapy seeds, for example, a radioactive microsphere available from 3M Company of St. Paul, Minn. Other suitable brachytherapy radiation sources include I-Plant™, (Med-Tec, Orange City, Iowa.).

The device 10 can be provided, at least in part, with a lubricious exterior coating, such as a hydrophilic material. The lubricious coating preferably is applied to the elongate shaft 11 or to the balloon 12 or both, to reduce sticking and friction during insertion and withdrawal of the device 10. Hydrophilic coatings such as those provided by AST, Surmodics, TUA Systems, Hydromer, or STS Biopolymers are suitable. The surfaces of the device 10 may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating may also be an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating may be provided on the elongated shaft of the delivery device 10 at the point where the device 10 enters the patient's skin.

The device 10 may be used to treat a body cavity of a patient in the manner described in the previously referred to co-pending applications. Usually the adapter 15 on the proximal end of the catheter device extends out of the patient during the procedure when the balloon is inflated. The catheter shaft 11 is preferably flexible enough along a length thereof, so that once the balloon is inflated to a turgid condition, the catheter shaft can be folded or coiled and secured to or placed under the patient's skin before the exterior opening of the treatment passageway to the treatment site is closed. At the end of the treatment time, e.g. 5-10 days, the exterior opening can be reopened and the catheter removed from the patient. See for example the discussion thereof in previously discussed co-pending application Ser. No. 11/357,274. The coiled or folded flexible shaft does not cause significant discomfort to the patient while secured to or under the patient's skin.

Typically, radiation balloon catheters for breast implantation are about 6 to about 12 inches in length. The catheter shaft is about 0.25 to about 0.4 inch (6.4-10.2 mm) transverse dimensions. The size of individual radiation lumens depends upon the size of the radiation source, but generally are about 0.02 to about 0.2 inch (0.5-5.1 mm), preferably about 0.04 to about 0.1 inch (1-2.5 mm). The inflation and vacuum lumens in the shaft are about 0.03 to about 0.0.08 inch (0.8-2 mm). The balloons are designed for inflated configurations about 0.5 to about 4 inches, typically about 1 to about 3 inches in transverse dimensions, e.g. diameters.

While particular forms of the invention have been illustrated and described herein, it will be apparent that various modifications and improvements can be made to the invention. To the extend not described herein, the various elements of the catheter device may be made from conventional materials used in similar devices and the design and size of various components may follow similar devices know in the art. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "manufacture", "portion", "section", "steps" and words of similar import when used herein shall not be construed as invoking the provisions of 35 U.S.C. §112(6) unless the following claims expressly use the terms "means for" or "step for" followed by a particular function without reference to a specific structure or action. All patents and all patent applications referred to above are hereby incorporated by reference in their entirety.

What is claimed is:

1. An elongated catheter device for irradiating tissue surrounding a body cavity within a patient, comprising:
   a. a treatment location on a distal portion of the catheter device;
   b. an elongated flexible shaft which has a longitudinal axis, which is formed at least in part of a low durometer polymeric material and which has a plurality of radiation delivery lumens extending about the longitudinal axis having surfaces formed of the low durometer polymeric material and configured to receive a radiation source; and
   c. each of said radiation delivery lumens having a coating that includes a polymeric solute material with a durometer substantially higher than the low durometer polymeric material of the flexible shaft that is deposited from a solution thereof onto the surfaces of said lumens so as to line said radiation delivery lumens and to provide improved frictional characteristics thereto.

2. The device of claim 1, wherein the low durometer material has a durometer hardness of about 70A to 25D Shore.

3. The device of claim 1, wherein the high durometer material has a durometer hardness of at least 40D Shore.

4. The device of claim 1, wherein the coating is formed by applying solution of the high durometer polymeric solute material in a non-aqueous solvent to the surface of the lumen, evaporating the solvent and leaving a layer of the high durometer polymeric solute material deposited on the lumen surface.

5. The device of claim 4, wherein the non-aqueous solvent is selected from the group consisting of tetrahydrofuran, cyclohexanone, dimethyl formamide, or a combination thereof.

6. The device of claim 4, wherein the solvent contains about 0.1 to about 5% (by wt.) high durometer polymeric material.

7. The device of claim 6, wherein the solvent contains about 0.5 to about 2% (by wt.) high durometer polymeric material.

8. The device of claim 6, wherein the high durometer polymeric material of a layer on the surface of the inner lumen has a Shore durometer hardness of about 50D to about 80D.

9. The device of claim 1, wherein an inflatable balloon surrounds at least part of the treatment location.

10. The device of claim 9, wherein the flexible elongated shaft has at least one inflation lumen extending therein to the treatment location and in fluid communication with the interior of the balloon.

11. The device of claim 9, wherein the balloon is configured to partially fill the body cavity when inflated to a turgid condition.

12. The device of claim 1, wherein the distal portion has a vacuum port and a vacuum lumen in fluid communication with the vacuum port.

13. The device of claim 12, wherein the vacuum lumen is configured to be in fluid communication with a vacuum source.

14. The device of claim 1, wherein a radiation source is slidably disposed within the radiation delivery lumen and configured to be disposed in the treatment location.

15. The elongated catheter device of claim 1 wherein the coating comprises pigment particles to provide an undulating or uneven coating surface which reduces contact with the radiation source and the friction between the radiation source and the coating.

16. The elongated catheter device of claim 15 wherein the pigment particles are selected from the group consisting of Reactive Blue, Prussian Blue, iron oxide, titanium dioxide, manganese violet and ultramarine blue.

17. The elongated catheter device of claim 1 wherein the improved frictional characteristics comprises reduced friction.

18. The elongated catheter device of claim 17 wherein the catheter has a friction reducing compound that is at least partially soluble in a solvent.

19. The elongated catheter device of claim 18 wherein the friction reducing compound is selected from the group consisting of mold release agents, surfactants and lubricants.

20. The elongated catheter device of claim 19 wherein the mold release agent is a zinc stearate.

21. The elongated catheter device of claim 19 wherein the surfactant is a polyvinyl alcohol.

22. The elongated catheter device of claim 19 wherein the lubricant is a Carnauba wax.

* * * * *